United States Patent
Dunbar et al.

(10) Patent No.: US 10,327,653 B2
(45) Date of Patent: *Jun. 25, 2019

(54) METHOD AND APPARATUS FOR HEART RATE MONITORING

(71) Applicant: TEXAS INSTRUMENTS INCORPORATED, Dallas, TX (US)

(72) Inventors: Steven T. Dunbar, Lafayette, CO (US); Sourabh Ravindran, Dallas, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/804,937

(22) Filed: Nov. 6, 2017

(65) Prior Publication Data

US 2018/0103855 A1    Apr. 19, 2018

Related U.S. Application Data

(63) Continuation of application No. 12/768,488, filed on Apr. 27, 2010, now Pat. No. 9,808,163.

(60) Provisional application No. 61/174,291, filed on Apr. 30, 2009.

(51) Int. Cl.
    *A61B 5/04*      (2006.01)
    *A61B 5/0245*    (2006.01)
    *A61B 5/00*      (2006.01)

(52) U.S. Cl.
    CPC .......... *A61B 5/0245* (2013.01); *A61B 5/7203* (2013.01); *A61B 5/7221* (2013.01); *A61B 5/7246* (2013.01)

(58) Field of Classification Search
    None
    See application file for complete search history.

(56) References Cited

U.S. PATENT DOCUMENTS

2010/0094150 A1    4/2010   Ravindran

OTHER PUBLICATIONS

"Multi-component based cross correlation beat detection in electrocardiogram analysis"; Biomed Eng Online V.3; 2004; Thorsten Las, Chris D Jugent and Frank J Owens.
"Zero-lag Correlation," http://wiki.seg.org/index.php/Dictionary;Zero-lag_correlation.

(Continued)

*Primary Examiner* — Eric D. Bertram
*Assistant Examiner* — Elizabeth K So
(74) *Attorney, Agent, or Firm* — Andrew Viger; Charles A. Brill; Frank D. Cimino

(57) ABSTRACT

A method and apparatus for monitoring heart rate. The method includes receiving a digital heart monitoring signal, determining the integrity of said signal with a "hand detect" signal that confirms electrical connection to the subject, dividing the digital heart monitoring signal into at least one frame, generating a folded correlation value for the center sample in the at least one frame, identify the number of peaks folded correlation values based on amplitude and distance parameters of the digital heart monitoring signal in the at least one frame, removing false peaks and collecting peaks corresponding to a length of time, determining the heart rate based on the identified peaks wherein the identified peaks relate to a minimum distance between valid heart beat peaks based on a heart rate estimate, computing the weighted average of heart rate value based on the number of previous heart rate values.

8 Claims, 2 Drawing Sheets

(56) References Cited

OTHER PUBLICATIONS

Lawrence R. Rabiner, "On the Use of Autocorrelation Analysis for Pitch Detection", IEEE Transactions on Acoustics, Speech, and Signal Processing, vol. ASSP-25, No. 1, Feb. 1977, pp. 24-33.
Murugavel Raju, "Heart-rate and ekg monitor using the msp430fg439," Texas Instruments Application Report, Sep. 2007.
Jung H. Lee, et al., "Fast Cross-Correlation Method for Real Time Detection of Fetal Heart Rate," Proceedings of the 20th Annual International Conference of the IEEE Engineering in Medicine and Biology Society, vol. 20, No. 1, 1998, pp. 178-181.
M.A. Khayer and M.A. Haque, "ECG Peak Detection Using Wavelet Transform," Dept. of Electrical and Electronic Engineering, BUET, Dhaka-1000, Bangladesh.

METHOD AND APPARATUS FOR HEART RATE MONITORING

CROSS-REFERENCE TO RELATED APPLICATIONS

This application is a continuation of U.S. patent application Ser. No. 12/768,488, filed Apr. 27, 2010 (U.S. Pat. No. 9,808,163), which claims benefit of U.S. provisional patent application Ser. No. 61/174,291, filed Apr. 30, 2009, which are incorporated by reference in their entirety.

BACKGROUND OF THE INVENTION

Field of the Invention

Embodiments of the present invention generally relate to a method and apparatus for electrocardiogram (ECG) based rate detection. More specifically, the ECG based rate detector functions in real-time, is low complexity and utilizes low-memory.

Description of the Related Art

Heart rate detection from electrocardiogram (ECG) signal has been well studied. Some methods proposed previously, detect the QRS complex peaks by high pass filtering and subtraction of a fixed threshold. This method, though straight forward has the disadvantage that it is not robust to variations in relative amplitude. Another technique proposes use of discrete wavelet transform to remove mean variations and other artifacts. The peaks corresponding to the R-waves are detected using slope detection and thresholding. Some of the other signal processing choices include adaptive filtering to remove artifacts, matched filtering to detect the QRS complex and frequency tracking.

SUMMARY OF THE INVENTION

Embodiments of the present invention relate to a method and apparatus for monitoring a heart rate. The method includes receiving a digital heart monitoring signal, dividing the digital heart monitoring signal into at least one frame, generating a folded correlation value for the center sample in the at least one frame, identify the number of peaks of the folded correlation values based on amplitude and distance parameters of the digital heart monitoring signal in the at least one frame, removing false peaks and collecting peaks corresponding to a length of time, determining the heart rate based on the identified peaks wherein the identified peaks relate to a minimum distance between valid heart beat peaks based on a heart rate estimate, computing the weighted average of heart rate value based on the number of previous heart rate values.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
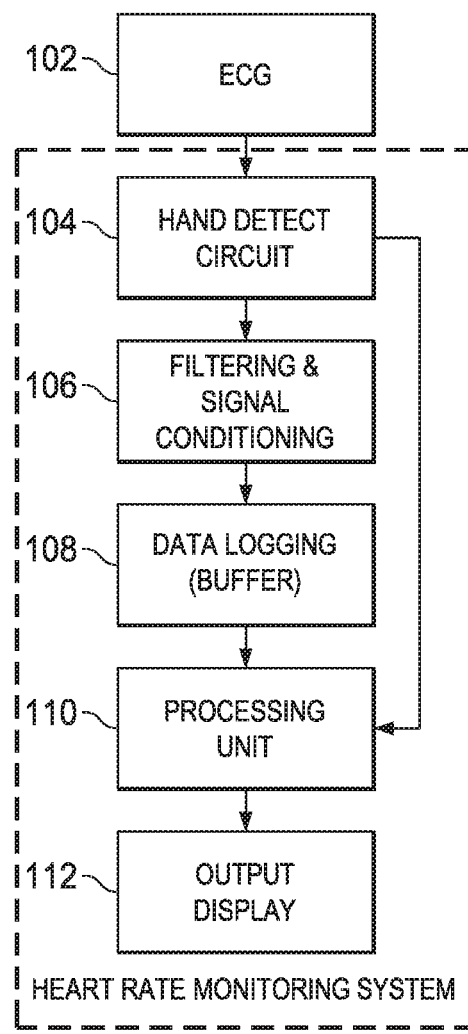
FIG. 1 is an embodiment depicting a block diagram for a heart rate monitoring system.

FIG. 1 is an embodiment depicting a block diagram for a heart rate monitoring system 100. The heart rate monitor system comprises an electrocardiogram (ECG) 102, a Hand detect circuit 104, a filtering signal conditioning unit 106, a data logging buffer 108, a processing unit 110, and an output display 112.

Herein, the proposed system 100 is a mixed analog and digital solution. The DC offset removal of the acquired signal is accomplished using a single-pole analog high-pass filter, i.e., with a cutoff frequency of 7 Hz. The signal is then passed through a low-pass filter with, i.e., a 27 Hz cut-off frequency to remove out-of-band noise. The analog front-end also provides sufficient gain to the acquired signal. The signal is then processed by a CPU. In one embodiment, a block processing algorithmic approach is utilized, which allows for a more efficient and accurate paradigm for heart rate detection from ECG 102. The approach also allows us to perform back-end signal processing to increase robustness of the proposed method.

The compact version of the proposed solution may run on as little as 128 bytes of RAM and 2 Kb of code space. In one embodiment, in the context of a fitness equipment (such as a treadmill), a hardware circuit, such as hand detect circuit 104, is utilized to detect the contact of the hand to the electrodes and generate a hand detect signal to gate the data logging and to trigger the heart rate processing algorithm. The analog front-end also provides filtering and amplification of the signal.

In one embodiment, the proposed system, unlike a sample-by-sample approach that uses thresholding or a similar approach to detect signal peaks, incoming data is buffered into blocks. Peak detection is accomplished by a simple maximum function. Further multiple blocks are then processed to weed out possible false peaks.

In another embodiment, P and T-wave components of the ECG 102 signal that may contribute to false peaks are removed using a difference operation. Further, the QRS peaks may be enhanced using a proprietary correlation based method.

In yet another embodiment, a time based approach may be used to correct for any false peaks that might have slipped through the previous stages. The timing parameter maybe updated on a continuous basis to enable tracking of changes in the heart rate.

The system consists of a hardware circuit that detects the presence of valid data and enables data logging. The detection circuit consists of a dual comparator with threshold voltage of, i.e., 410 mV. The output of the comparator is used to generate a pulse that begins or terminates data logging.

The signal path consists of a filtering and signal conditioning unit 106 that may act as an amplifier to provide gain while rejecting line noise due to its high common mode rejection, a high-pass filter for DC removal and a low-pass filter to reject high frequency noise. The signal is then fed to a mixed signal microcontroller, i.e., MSP430. The algorithm for computing the heart rate is implemented in the microcontroller.

In the proposed system 100, incoming data maybe buffered into frames in buffer 108. Each of these frames is subjected to a difference function which removes the mean as well as low frequency components from the signal. The frame is then processed, in processing unit 110. The processing unit 110 may use a folded correlation method to enhance the R peaks. The resulting signal is then subjected to a maximum function, which may pick peaks within each frame. Peaks over 5 seconds, for example, are collected and subjected to post processing. During post processing, peaks with relatively small amplitudes and small distance (time) separation are discarded. In order to save memory the difference of the peak locations are stored rather than the peaks locations themselves (the difference in peak location can be stored in a byte whereas peak locations could potentially be of word length). A timing based check is used to correct for any false peaks.

The heart rate obtained from the 5 second segment, for example, is subjected to a weighted average over the past, i.e., 4 heart rate values. The resulting value is the reported heart rate for last added frame. The information pertaining to the oldest frame is discarded and a new frame is added to obtain the next estimate. The algorithm is capable of outputting heart rate values for every 1 second, for example. The resulting signal may be displayed on output display 112 or stored for future display.

Figure 2:
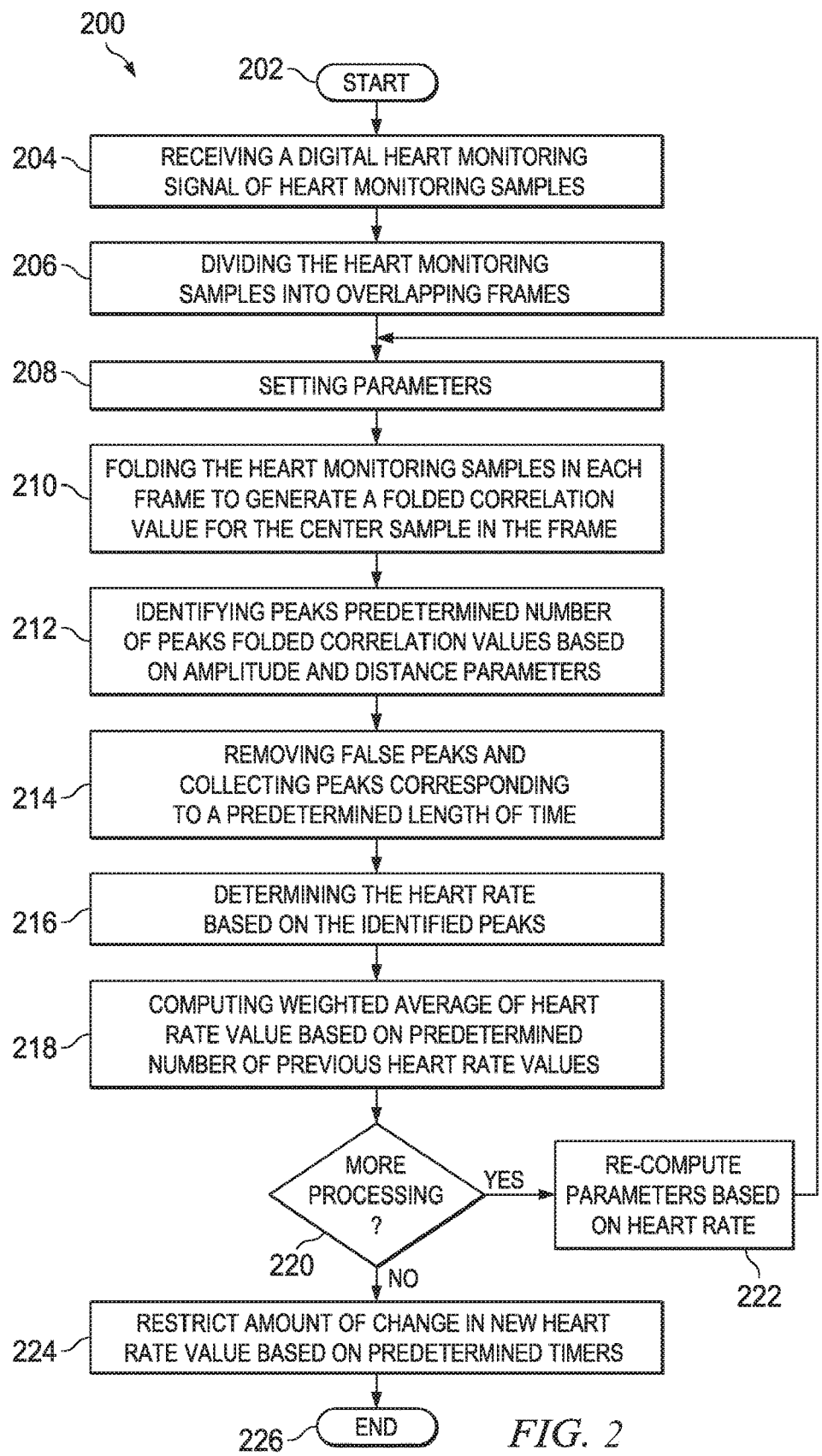
FIG. 2 is a flow diagram depicting an embodiment of a method for monitoring a heart rate in accordance with the present invention.

FIG. 2 is a flow diagram depicting an embodiment of a method 200 for monitoring a heart rate in accordance with the present invention. The method 200 starts at step 202 and proceeds to step 204. At step 204, the method 200 receives a digital heart monitoring signal of a heart monitoring samples. At step 206, the method divides the heart monitoring samples into overlapping frames. At step 208, the method 200 may set parameters to prepare for step 210. Such parameters may include minimum distance between valid heart beat peaks based on the current estimate of the heart rate value. At step 210, the method 200 may utilize the parameters of step 208 to fold the heart monitoring samples in frames to generate a folded correlation value for the center sample in the frame. At step 212, the method 200 identifies peaks. For example, the method 200 may identify a predetermined number of peaks of folded correlation values based on amplitude and distance parameters. At step 214, the method 200 removes false peaks and collects peaks corresponding to a length of time, which maybe predetermined. At step 216, the method 200 determines the heart rate based on the identified peaks. At step 218, the method 200 computes weighted average of heart rate value based on predetermined number of previous heart rate values. At step 220, the method 200 determines if more processing is required. If more processing is required, the method 200 proceeds to step 222 to re-compute parameters based on heart rate and proceeds to step 208. Otherwise, at step 224, the method 200 restricts the amount of change in the new heart rate value based on a predetermined timer. The method proceeds to step 226, wherein the method 200 ends.

In one embodiment, the hand detect is used to start or stop data logging, and/or reinitialize the processor unit and instrumentation amplifier to fixed initial values. This provides a convenient reset mechanism and more accurate response when the subject's ECG signal is removed and reapplied. In another embodiment, a timer is set to determine the change in the current heart rate value. For example, initially the heart rate value maybe allowed to change more rapidly to minimize the settling time. After the expiration of the timer, the heart rate values maybe allowed to change less rapidly. In some embodiment, a second timer is utilized to allow for the heart rate to settle before using the heart rate value to set parameters.

While the foregoing is directed to embodiments of the present invention, other and further embodiments of the invention may be devised without departing from the basic scope thereof, and the scope thereof is determined by the claims that follow.

What is claimed is:

1. A method for monitoring a heart rate, comprising:
receiving ECG (electrocardiogram) signals;
converting the ECG signals to a digital heart monitoring signal as a sequence of heart monitoring samples;
receiving at a processor the digital heart monitoring signal;
dividing the digital heart monitoring signal into successive overlapping frames, each with an odd number N of samples, and each frame encompassing multiple heart beats;
setting distance parameters corresponding to a minimum distance between valid heart beat peaks based on a current estimate of heart rate;
processing a current frame using the distance parameters by:
generating a folded correlation value for a center sample based on a folded correlation of (N−1)/2 samples preceding a center sample, and time-reversed (N−1)/2 samples following the center sample;
identifying a number of peaks of the folded correlation values, using the distance parameter parameters;
removing false peaks using the distance parameter, to obtain identified peaks;
determining the current heart rate based on the identified peaks; and
computing a weighted average heart rate based on a predetermined number of previous heart rates, each computed from a respective frame;
restricting a change in heart rate from the current frame to the next frame based on a predetermined timer; and
generating heart rate signals corresponding to the determined current heart rate.

2. The method of claim 1, wherein identifying the number of peaks is accomplished using the distance parameters and amplitude parameters.

3. The method of claim 1, further comprising:
selectively updating the distance parameter in preparation for processing a next frame.

4. The method of claim 2, further comprising:
selectively updating the amplitude parameter in preparation for processing a next frame.

5. An apparatus for monitoring a heart rate, comprising:
means for receiving ECG (electrocardiogram) signals;
means for converting the ECG signals to a digital heart monitoring signal as a sequence of heart monitoring samples;
processing means for processing the digital heart monitoring signal, by:
means for dividing the digital heart monitoring signal into successive overlapping frames, each with an odd number N of samples, and each frame encompassing multiple heart beats;
setting distance parameters corresponding to a minimum distance between valid heart beat peaks based on a current estimate of heart rate;
means for processing a current frame using the distance parameters, including generating a folded correlation value for a center sample based on a folded correlation of (N−1)/2 samples preceding a center sample, and time-reversed (N−1)/2 samples following the center sample;

identifying a number of peaks of the folded correlation values, using the distance parameter;

removing false peaks using the distance parameter, to obtain identified peaks;

determining the current heart rate based on the identified peaks; and computing a weighted average heart rate based on a predetermined number of previous heart rates, each computed from a respective frame;

restricting a change in heart rate from the current frame to the next frame based on a predetermined timer; and generating heart rate signals corresponding to the determined current heart rate.

6. The apparatus of claim 5, wherein identifying the number of peaks is accomplished using the distance parameters and amplitude parameters.

7. The apparatus of claim 5, the processing means further operable to:

selectively updating the distance parameter in preparation for processing a next frame.

8. The apparatus of claim 5, the processing means further operable to:

selectively updating the amplitude parameter in preparation for processing a next frame.

* * * * *